United States Patent [19]

Müller et al.

[11] Patent Number: 4,657,707

[45] Date of Patent: Apr. 14, 1987

[54] PROCESS FOR THE PREPARATION OF AROMATIC HYDROXY COMPOUNDS

[75] Inventors: Rolf Müller, Aesch; Maurice Grélat, Bettingen, both of Switzerland

[73] Assignee: Ciba-Geigy Corporation, Ardsley, N.Y.

[21] Appl. No.: 736,911

[22] Filed: May 22, 1985

[30] Foreign Application Priority Data

May 29, 1984 [CH] Switzerland ............. 2633/84

[51] Int. Cl.[4] .............. C07C 50/18; C07C 50/12; C07C 39/04
[52] U.S. Cl. ........................ 260/383; 260/396 R; 260/381; 568/716
[58] Field of Search ............ 260/383, 396 R, 381; 568/716, 376, 764

[56] References Cited

U.S. PATENT DOCUMENTS

| | | | |
|---|---|---|---|
| 3,031,466 | 4/1962 | Budziarek et al. | 260/383 |
| 3,562,299 | 2/1971 | Harvey | 260/383 |
| 3,636,008 | 1/1972 | Yamada et al. | 260/383 |
| 3,821,262 | 6/1974 | Schoenauber et al. | 260/383 |
| 3,880,892 | 4/1975 | Hiller et al. | 260/380 |
| 4,292,247 | 9/1981 | Nishikuri et al. | 260/381 |

FOREIGN PATENT DOCUMENTS 203083 12/1906 Fed. Rep. of Germany ...... 260/383

OTHER PUBLICATIONS

Japanese Application No. 26,831/65 Abstract (Derwent Jap. Pat. Rep., vol. 4, No. 47, 28.12.65).

*Primary Examiner*—Richard L. Raymond
*Assistant Examiner*—Raymond Covington
*Attorney, Agent, or Firm*—Edward McC. Roberts; Kevin T. Mansfield; Irving M. Fishman

[57] ABSTRACT

The invention relates to a process for the preparation of aromatic hydroxy compounds, starting from the corresponding halogenated aromatic compounds and replacing the halogen atom or atoms by the hydroxyl group. The process comprises converting the halogenated aromatic compound into the hydroxy compound by treatment with concentrated sulfuric acid, with the addition of an aldehyde and at elevated temperature.

The aromatic hydroxy compounds are used as intermediates, for example for the manufacture of disperse and vat dyes.

8 Claims, No Drawings

PROCESS FOR THE PREPARATION OF AROMATIC HYDROXY COMPOUNDS

The present invention relates to a process for the preparation of monocyclic or polycyclic aromatic compounds containing at least one hydroxyl group, starting from corresponding halogenated aromatic compounds, by replacing the halogen atom or atoms by the hydroxyl group.

It is known to replace all or some of the halogen atoms of haloanthraquinones by the hydroxyl group by treating the haloanthraquinones in question with fuming sulfuric acid, with the addition of boric acid, in the temperature range of about 140° C. The drawback of this process, which is employed technically, is that it is very difficult to regenerate the sulfuric acid, as the sulfuric acid combines with the boric acid to form glassy products, thereby making the process uneconomic.

A novel process has now been developed which rectifies this shortcoming and substantially facilitates the regeneration of the sulfuric acid and which, in addition, can be carried out at low temperature.

The novel process of this invention comprises treating halogenated monocyclic or polycyclic aromatic compounds with concentrated sulfuric acid, with the addition of an aldehyde and at elevated temperature, to replace all or some of the halogen atoms by the hydroxyl group. Concentrated sulfuric acid in the present context will be understood as meaning sulfuric acid having a concentration of 70 to 100% by weight, preferably of 98 to 100% by weight (sulfuric acid monohydrate). In addition, the concentrated sulfuric acid may also contain up to about 25% by weight of sulfur trioxide (oleum).

Suitably, the aldehydes which may be employed in process of this invention are both aliphatic as well as aromatic aldehydes. It is preferred to use aliphatic aldehydes, in particular those that contain 1 to 4 carbon atoms in their monomolecular form. Among these, formaldehyde in its monomeric or polymeric form (paraformaldehyde), or a formaldehyde donor such as urotropin or paraldehyde, are particularly suitable. Other suitable aldehydes are, for example, acetaldehyde, propionaldehyde, n-butyraldehyde and isobutyraldehyde. Good results are obtained when using benzaldehyde or p-chlorobenzaldehyde as aromatic aldehyde.

The aldehyde will be employed in amounts of 0.25 to 6 equivalents, preferably of 0.5 to 2 equivalents, based on the starting compound, namely the halogenated monocyclic or polycyclic aromatic compound.

The temperature range in which the process of this invention is carried out is preferably from 50° to 200° C., most preferably from 100° to 150° C. Depending on the starting material and reaction temperature, the reaction time is normally from about 2 to 10 hours.

The process of this invention, which is preferably carried out under anhydrous conditions (100% sulfuric acid as reaction medium and in an inert gas atmosphere), is particularly suitable for the preparation of hydroxyanthraquinones from the corresponding haloanthraquinones or derivatives thereof. Such compounds have, for example, the formula

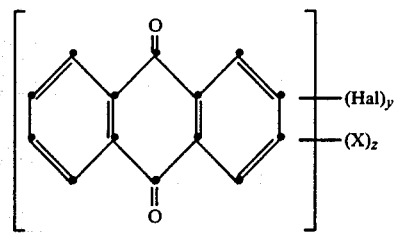

wherein Hal is a halogen atom, preferably Cl or Br, X is hydrogen, $NH_2$, acylamino or, preferably, acetylamino, or is OH, and y and z are each 1 or 2.

Representative examples of suitable starting materials are: 1,5-diacetylamino-4,8-dibromoanthraquinone, 1-amino-2,4-dichloroanthraquinone, 1-amino-2,4-dibromoanthraquinone and 1-chloro-4-hydroxyanthraquinone.

Further, the process of this invention is suitable for the preparation of e.g. 1,4-dihydroxybenzene (hydroquinone) from p-chlorophenol, and of 2,3-dihydroxynaphthoquinone from 2,3-dichloronaphthoquinone.

Depending on, in particular, the temperature and the concentration of aldehyde, all or only some of the halogen atoms are replaced by the hydroxyl group in the process of this invention.

The hydroxy compounds obtained are valuable intermediates for the manufacture of dyes, in particular disperse dyes and vat dyes. They are obtained by the process of this invention in high yield (over 90%, depending on the educt).

The invention is illustrated by the following Examples, in which parts and percentages are by weight. Analysis by thin-layer chromatography is carried out on silica gel plates with UV indicator.

EXAMPLE 1

A stirred reactor is charged with 184 parts of sulfuric acid monohydrate and 4.8 parts (1 equivalent) of paraformaldehyde are added, with stirring, over about 15 minutes. Stirring is continued until a solution is obtained. This solution is then heated to 60°–65° C. and 46.5 parts of 98% 1-amino-2,4-dichloroanthraquinone are added. The reaction mixture is heated for 1 hour to 110° C. and this temperature is maintained for 3 hours. The mixture is cooled to 100° C. and 870 parts of water are added. The resultant suspension is heated to 90°–95° C. and stirred for 2 hours at this temperature, then cooled and filtered. The filter cake is washed with hot water and the product is dried in vacuo at 80°–90° C., affording 43.3 parts (95% yield) of 1-amino-2-chloro-4-hydroxyanthraquinone. $R_f=0.29$ (eluant: concentrated formic acid, saturated with 1-bromonaphthalene).

EXAMPLE 2

A stirred reactor is charged with 184 parts of sulfuric acid monohydrate and 4.2 parts (0.8 equivalent) of paraformaldehyde are added, with stirring, over about 15 minutes. The mixture is stirred until a clear solution is obtained. This solution is heated to 60°–65° C. and then 59.5 parts of 1-amino-2,4-dibromoanthraquinone (96% pure) are added.

The reaction mixture is then heated to 110° C. over 1 hour and stirred at this temperature for a further 4 hours. During the reaction, nitrogen is passed through the reaction mixture, which is subsequently cooled to 60° C. Then 120 parts of water are added and the resultant suspension is filtered. The filter residue is washed with hot water until neutral and the product is dried in vacuo at 80°–90° C. Yield: 48.5 parts (93% of theory) of 1-amino-2-bromo-4-hydroxyanthraquinone. $R_f$=0.27 (eluant: concentrated formic acid, saturated with 1-bromonaphthalene).

EXAMPLE 3

A stirred reactor is charged with 184 parts of sulfuric acid monohydrate and 43.8 parts (2 equivalents) of 4-chlorobenzaldehyde are added, with stirring, over about 15 minutes.

The reaction mixture is then heated to 60°–65° C. and 46.5 parts of 98% 1-amino-2,4-dichloroanthraquinone are added. The reaction mixture is then heated to 140° C. over 1 hour and kept at this temperature for 6 hours. The mixture is then cooled to 100° C. and 870 parts of water are added. The resultant suspension is heated to 90°–95° C. and stirred for 2 hours at this temperature, then cooled and filtered. The filter residue is washed with hot water and the product is dried in vacuo at 80°–90° C. The crude product consists substantially of 1-amino-2-chloro-4-hydroxyanthraquinone; $R_f$=0.29 (eluant: see Example 1).

Employing the same reaction conditions, 1-amino-2-chloro-4-hydroxyanthraquinone is also obtained by using the same amount of benzaldehyde instead of chlorobenzaldehyde.

EXAMPLE 4

A stirred reactor is charged with 18.4 parts of sulfuric acid monohydrate and 0.48 part of paraformaldehyde are added, with stirring, over about 15 minutes. Stirring is continued until a solution is obtained. This solution is then heated to 60°–65° C. and 4.3 parts of 1-chloro-4-hydroxyanthraquinone are added. The reaction mixture is heated for 1 hour to 140° C. and this temperature is maintained for 6 hours. The reaction mixture is then poured into 100 parts of water and the precipitate is isolated by filtration. The filter cake is washed until neutral and the resultant 1,4-dihydroxyanthraquinone (quinizarine) is dried in vacuo at 80°–90° C.; $R_f$=0.91 (eluant: toluene saturated with concentrated formic acid).

EXAMPLE 5

A stirred reactor is charged with 184 parts of sulfuric acid monohydrate and 20.1 parts of 4-chlorophenol and then 4.7 parts of paraformaldehyde are added, with stirring, at room temperature. The mixture is heated to 100° C. and kept at this temperature for 3 hours. The reaction mixture is then cooled to 30° C. and poured into 870 parts of water. Filtration yields a strongly acidic crude aqueous product containing about 50% of hydroquinone; $R_f$=0.54 (eluant: benzene/ethyl acetate 9:1).

What is claimed is:

1. A process for the preparation of a hydroxy substituted anthraquinone, naphthoquinone or phenol compound, starting from a corresponding halogenated compound and replacing the halogen atom or atoms by a hydroxyl group, which process comprises reacting a halogenated anthraquinone, naphthoquinone or phenol compound with concentrated sulfuric acid, with the addition of an aldehyde, at a temperature of 50° to 200° C.

2. A process according to claim 1, wherein sulfuric acid having a concentration of 70 to 100% is used.

3. A process according to claim 1, wherein sulfuric acid having a concentration of 98 to 100% is used.

4. A process according to claim 1, wherein the aldehyde employed is acetaldehyde, propionaldehyde, n-butyraldehyde, i-butyraldehyde, benzaldehyde or p-chlorobenzaldehyde.

5. A process according to claim 4, wherein formaldehyde in its monomeric or polymeric form, or a formaldehyde donor, is employed as aldehyde.

6. A process according to claim 1, wherein 0.25 to 6 equivalents of aldehyde are used, based on the halogenated compound.

7. A process according to claim 6, wherein 0.5 to 2 equivalents of aldehyde are used, based on the halogenated compound.

8. A process according to claim 4, wherein the reaction is carried out in the temperature range from 100° to 150° C.

* * * * *